United States Patent
Sato

(10) Patent No.: US 7,642,198 B2
(45) Date of Patent: Jan. 5, 2010

(54) METHOD FOR EVALUATING CRYSTAL DEFECTS OF SILICON WAFER

(75) Inventor: Hideki Sato, Gunma (JP)

(73) Assignee: Shin-Etsu Handotai Co., Ltd., Tokyo (JP)

(*) Notice: Subject to any disclaimer, the term of this patent is extended or adjusted under 35 U.S.C. 154(b) by 2 days.

(21) Appl. No.: 10/594,458

(22) PCT Filed: Mar. 11, 2005

(86) PCT No.: PCT/JP2005/004294
§ 371 (c)(1),
(2), (4) Date: Sep. 26, 2006

(87) PCT Pub. No.: WO2005/093818
PCT Pub. Date: Oct. 6, 2005

(65) Prior Publication Data
US 2007/0204789 A1    Sep. 6, 2007

(30) Foreign Application Priority Data
Mar. 29, 2004    (JP) .............................. 2004-095864

(51) Int. Cl.
*H01L 21/302* (2006.01)
(52) U.S. Cl. ................... 438/753; 438/745; 216/99
(58) Field of Classification Search .......... 438/74, 438/750, 752, 745, 12, 753; 252/79.1, 79.2; 216/84, 99, 106
See application file for complete search history.

(56) References Cited

U.S. PATENT DOCUMENTS

| | | | | |
|---|---|---|---|---|
| 3,558,375 | A * | 1/1971 | Engeler | 438/379 |
| 3,772,102 | A * | 11/1973 | Tiemann et al. | 430/323 |
| 3,960,623 | A * | 6/1976 | Gantley | 438/745 |
| 4,251,300 | A * | 2/1981 | Caldwell | 438/363 |
| 5,409,569 | A * | 4/1995 | Seki et al. | 216/99 |
| 5,714,407 | A * | 2/1998 | Maeno et al. | 438/701 |
| 6,068,788 | A | 5/2000 | Kezuka et al. | |
| 6,768,175 | B1 | 7/2004 | Morishita et al. | |
| 2002/0167661 | A1 | 11/2002 | Yagi | |

FOREIGN PATENT DOCUMENTS

| | | |
|---|---|---|
| JP | A-04-209532 | 7/1992 |
| JP | B2-06-103714 | 12/1994 |
| JP | A-07-263429 | 10/1995 |

(Continued)

*Primary Examiner*—Lan Vinh
(74) *Attorney, Agent, or Firm*—Oliff & Berridge, PLC

(57) ABSTRACT

A method for evaluating crystal defects of a silicon wafer comprising: etching a surface of the silicon wafer by immersing the wafer in an etching solution; and observing etch pits formed on the etched surface of the wafer, wherein the silicon wafer of which crystal defects are evaluated has low electrical resistivity of 1 Ω·cm or less, and the etching solution is a mixture of hydrofluoric acid, nitric acid, acetic acid and water further including iodine or iodide, in which a volume ratio of nitric acid in the etching solution is the largest among volume ratios of hydrofluoric acid, nitric acid, acetic acid and water, and the etching solution is adjusted to have an etching rate of 100 nm/min or less for the silicon wafer. Thereby, there is provided a method for evaluating crystal defects of a silicon wafer with low electrical resistivity by using a chromium-free etching solution without toxic chromium with high capability of detecting defects.

2 Claims, 3 Drawing Sheets

FOREIGN PATENT DOCUMENTS

| | | |
|---|---|---|
| JP | A-11-238773 | 8/1999 |
| JP | A-2000-340541 | 12/2000 |
| JP | A-2002-25972 | 1/2002 |
| JP | A-2004-235350 | 8/2004 |
| JP | A-2004-279366 | 10/2004 |
| WO | WO 97/18582 | 5/1997 |
| WO | WO 00/19500 A1 | 4/2000 |
| WO | WO 01/48810 A1 | 7/2001 |

\* cited by examiner

METHOD FOR EVALUATING CRYSTAL DEFECTS OF SILICON WAFER

TECHNICAL FIELD

The present invention relates to a method for evaluating crystal defects of a silicon wafer, more particularly, to a method for evaluating crystal defects of a silicon wafer with low electrical resistivity including etching the silicon wafer and observing etch pits formed on the wafer surface.

BACKGROUND ART

Significantly larger packing densities of semiconductor integrated circuits have been achieved through the years. To obtain integrated circuits with high characteristics, reliability, and yield, not only high mechanical precision but also high electrical properties have come to be demanded. With this tendency, more rigorous conditions are imposed to crystal quality of a silicon wafer used for semiconductor integrated circuits. And to produce a silicon wafer with high crystal quality is demanded. Consequently, it is necessary to evaluate crystal quality of a silicon wafer accurately.

There is a selective etching method which is a method for evaluating crystal quality of a silicon wafer, in particular, a method for evaluating crystal defects of the wafer. In the method, Secco solution containing potassium dichromate (for example, see Japanese publication of examined application No. H06-103714), Sirtl solution or Wright solution containing chromic acid is used to conduct selective etching which utilizes difference of etching rates for a silicon wafer surface originated from the presence or absence of crystal defects. Then, etch pits appearing on the etched wafer surface are observed with an optical microscope etc. Thus the etch pits are detected and evaluated as crystal defects.

However, above etching solutions contain chromium. Chromium is a toxic substance, and wastewater treatment turns into a problem. Then, the so-called chromium-free etching solution containing no chromium is developed (see Japanese Patent Laid-open (Kokai) No. H07-263429; and Japanese Patent Laid-open (Kokai) No. H11-238773).

Besides, when a surface of a silicon wafer is etched with the etching solution containing chromium or the chromium-free etching solution as above, an etching rate is relatively high of 1 μm/min or more. Then, a silicon wafer with high electrical resistivity of greater than 1 Ω·cm is etched with such etching solutions, and etch pits are formed on a surface of the wafer. Thus the etch pits can be observed easily with an optical microscope etc.

However, for example, when a silicon wafer with low electrical resistivity of 1 Ω·cm or less undergoes selective etching as above, the following problem occurs: An unsaturated oxide film or stains (a stain film) is formed on the etched wafer surface significantly. And etch pits which must have been formed by selective etching cannot be observed.

Then, to observe the etch pits formed on a silicon wafer with low electrical resistivity of 1 Ω·cm or less, dilution etching method can be used. Dilution etching method uses an etching solution in which Secco solution or Wright solution as above is diluted with pure water etc. However, the dilution etching method uses an etching solution, although being diluted, still containing chromium which is a toxic substance as mentioned above. Therefore, a good deal of thought should be given to the influence on the global environment or humans, and wastewater treatment.

Besides, the following method can be conceived: diluting the chromium-free etching solution disclosed in Japanese Patent Laid-open (Kokai) No. H07-263429 and Japanese Patent Laid-open (Kokai) No. H11-238773 with water as with above to reduce an etching rate and to etch a silicon wafer with low electrical resistivity with this etching solution. However, simply diluting the chromium-free etching solution with water deteriorates selectivity of etching. And the capability to detect etch pits originated from crystal defects is deteriorated. Therefore, a problem occurs that it becomes extremely difficult to evaluate accurately crystal defects of a silicon wafer with low electrical resistivity.

Then, to circumvent these problems, not using selective etching method, a method for measuring crystal defects with an optical technique using light scattering (LST: Light Scattering Tomography) is also developed. However, the measuring method with LST has problems that measuring devices cost much and handling of the devices is difficult.

DISCLOSURE OF THE INVENTION

The present invention is accomplished in view of the aforementioned problems, and its object is to provide a method for evaluating crystal defects of a silicon wafer with low electrical resistivity with a chromium-free etching solution without toxic chromium and with high capability of detecting crystal defects.

In order to achieve the aforementioned object, according to the present invention, there is provided a method for evaluating crystal defects of a silicon wafer comprising: etching a surface of the silicon wafer by immersing the wafer in an etching solution; and observing etch pits formed on the etched surface of the wafer, wherein the silicon wafer of which crystal defects are evaluated has low electrical resistivity of 1 Ω·cm or less, and the etching solution is a mixture of hydrofluoric acid, nitric acid, acetic acid and water further including iodine or iodide, in which a volume ratio of nitric acid in the etching solution is the largest among volume ratios of hydrofluoric acid, nitric acid, acetic acid and water, and the etching solution is adjusted to have an etching rate of 100 nm/min or less for the silicon wafer.

Evaluating crystal defects of a silicon wafer with low electrical resistivity of 1 Ω·cm or less by etching a surface of the wafer with the above etching solution prevents forming an unsaturated oxide film or stains (a stain film) on the surface of the silicon wafer in etching. In addition, selectivity of etching is high. Therefore, crystal defects of a silicon wafer with low electrical resistivity are detected with excellent capability of detecting the defects, and the defects are evaluated accurately. Furthermore, the etching solution does not contain chromium, it is not necessary to consider the influence on the global environment and humans, wastewater treatment, and so on. Thus crystal defects of a silicon wafer with low electrical resistivity can be evaluated easily and conveniently.

In the above case, it is preferable that the etching solution includes hydrofluoric acid nitric acid:acetic acid:water in a volume ratio of 1:13-17:4-8:4-8.

The etching solution adjusted to include hydrofluoric acid, nitric acid, acetic acid, and water in the ratio has a proper etching rate and excellent selectivity. Etching a silicon wafer with low electrical resistivity with such an etching solution enables evaluation of crystal defects of the wafer with efficiency and with high accuracy.

Furthermore, it is preferable that the etching solution includes iodine or iodide in a range from 0.01 g to 0.09 g per 1 liter of total liquid volume of the etching solution.

Use of such an etching solution including iodine or iodide in the range prevents certainly generation of an unsaturated oxide film or stains (a stain film) on the wafer surface during etching. In addition, the present inventors have found that an etching rate of the etching solution including iodine or iodide varies considerably depending on a content of iodine or iodide. An etching rate of the etching solution including iodine or iodide in the range can be reduced easily to 100 nm/min or less.

In addition, it is preferable that a removal amount of the surface of the silicon wafer by etching is 50 nm or more.

Etching the surface of the silicon wafer with a removal amount of 50 nm or more enables forming etch pits certainly on the wafer surface originated from crystal defects. The etch pits can be observed easily and accurately with an optical microscope, and so on. Therefore, crystal defects of the silicon wafer can be evaluated accurately with stability.

According to the present invention, there is provided a method for evaluating crystal defects of a silicon wafer with low electrical resistivity by etching the wafer with a chromium-free etching solution with sensitivity equal to or better than conventional etching solutions containing chromium and with a low etching rate for silicon without generating an unsaturated oxide film or stains. Use of such a method for evaluating crystal defects according to the present invention enables detecting crystal defects in the vicinity of a surface of a silicon wafer with low electrical resistivity with high capability to detect the defects and evaluating the defects accurately without considering the influence on the global environment or humans, and wastewater treatment.

BEST MODE FOR CARRYING OUT THE INVENTION

Figure 1:
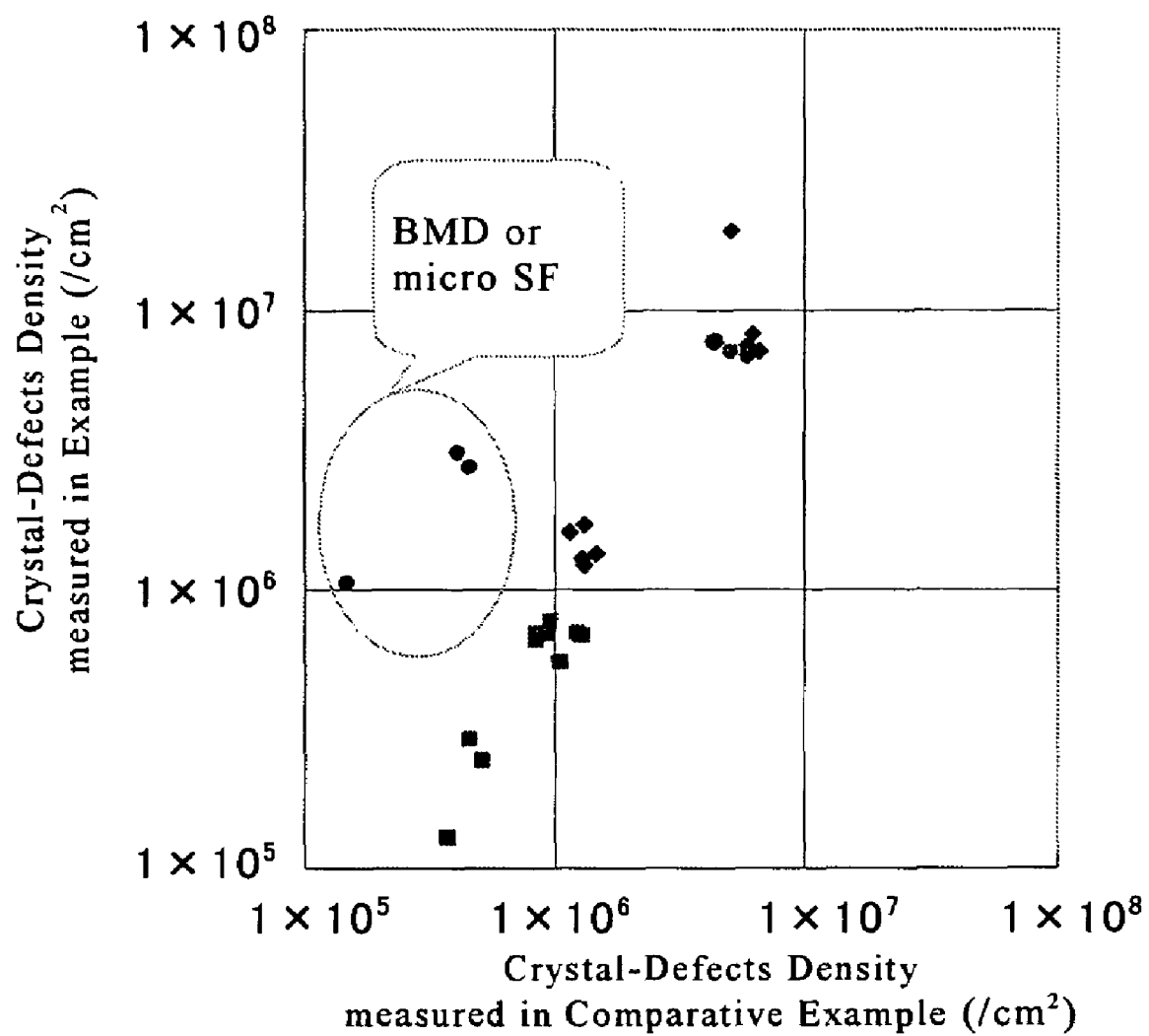
FIG. 1 is a graph in which a correlation between crystal defects density measured in Example and crystal defects density measured in Comparative Example is plotted.

Hereinafter, embodiments of the present invention will be explained. However, the present invention is not limited thereto.

The present inventors contemplated the use of an etching solution of mixed acid without chromium which is toxic to the global environment and humans as an etching solution for evaluating crystal defects of a silicon wafer with low electrical resistivity. At this time they considered that it was necessary to prevent forming an unsaturated oxide film or a stain film on a surface of a wafer in etching without deteriorating the capability to detect crystal defects. Because a conventional diluted etching solution obtained by a method for simply diluting an etching solution with pure water has a problem that selectivity of the etching solution is deteriorated and the capability to detect crystal defects is deteriorated.

Then, the present inventors studied and investigated thoroughly. As a result, they have conceived as follows to satisfy the necessity: adding iodine or iodide having an effect of preventing formation of an unsaturated oxide film or a stain film to an etching solution; increasing a ratio of nitric acid which is an oxidizing agent, and has a effect to increase an oxidizing rate at defect sites to enhance selectivity of etching; and also decreasing an etching rate of the etching solution. Thus, they have accomplished the present invention based on the following experimental results.

EXPERIMENT 1

First, an etching solution in which a volume ratio of nitric acid is increased to enhance selectivity of etching was prepared. With the etching solution, selective etching was conducted to a silicon wafer with low electrical resistivity.

The selective etching solution disclosed in the Japanese Patent Laid-open (Kokai) No. H07-263429 includes hydrofluoric acid (concentration of 50 wt %): nitric acid (concentration of 61 wt %) in a volume ratio of 1:12 even when the nitric acid ratio is the highest. Then, the following etching solution was prepared in the Experiment: Initially, an etching solution included hydrofluoric acid:nitric acid in a volume ratio of 1:15 to enhance selectivity of etching; Then, the etching solution included acetic acid (concentration of 99.7%) and water both of which were diluted threefold to hydrofluoric acid; That is, the etching solution included hydrofluoric acid:nitric acid:acetic acid:water in a volume ratio of 1:15:3:3 (Hereinafter, a ratio of these four components are always shown in this order); To 8 liters of this etching solution, 20 ml of KI solution (16.6 g of KI is dissolved in 1 liter of water) was added as an inhibitor of forming a stain film; Thus an etching solution to be used was prepared (Experimental Example 1). Next, with the etching solution, a silicon wafer with low electrical resistivity was etched and an etching rate was measured.

The wafer etched above is a p-type CZ silicon single crystal wafer with crystal orientation <100>, electrical resistivity of 0.01-1 Ω·cm, and oxygen concentration of 15-25 ppma. Incidentally, the value of oxygen concentration is calculated with the conversion factor of JEIDA (Japanese Electronic Industry Development Association; present JEITA) by infrared absorption method.

A surface of the silicon wafer with low electrical resistivity was etched with the etching solution of Experimental Example 1. It was confirmed that an unsaturated oxide film or a stain film was not generated, and etch pits were formed. However, roughening of the etched wafer surface was generated, and it was difficult to detect crystal defects with stability. In addition, an etching rate of the etching solution of Experimental Example 1 was measured. As a result, it was found that the etching rate was extremely high of approximately 1.54 μm/min though the etching solution of Experimental Example 1 included each component in a volume ratio of 1:15:3:3 in which the solution was diluted by trebling the water ratio of the selective etching solution of the Japanese Patent Laid-open (Kokai) No. H07-263429.

For comparison, the following etching solution (a diluted Secco solution) was prepared as an example of a diluted Secco solution used for evaluating crystal defects of a silicon wafer conventionally: hydrofluoric acid (concentration of 50 wt %), nitric acid (concentration of 61 wt %) and a solution containing chromium (a solution of 1.6 liter containing 10 g of $K_2Cr_2O_7$ and 40 g of $Cu(NO_3)_2 \cdot 3H_2O$) were mixed in a volume ratio of 1:1.6:3.2. And an etching rate of the diluted Secco solution was measured and it was approximately 0.065 μm/min (65 nm/min).

Then, to reduce the etching rate of the etching solution of Experimental Example 1, the following etching solution (Experimental Example 2) was prepared: The volume ratios of acetic acid and water were doubled as compared with the etching solution of Experimental Example 1; That is, the etching solution of Experimental Example 2 included each component in a volume ratio of 1:15:6:6. An etching rate of thus obtained etching solution was measured and it was approximately 0.023 μm/min (23 nm/min) Consequently, it was found that the etching rate can be reduced to a half of the rate of the diluted Secco solution or lower.

Furthermore, to investigate how the volume ratio of nitric acid or hydrofluoric acid influences the etching rate, the following etching solutions were prepared and an etching rate of each etching solution was measured: an etching solution in which the volume ratio of nitric acid was increased (a volume ratio of 1:30:3:3, Experimental Example 3); and an etching solution in which the volume ratio of hydrofluoric acid was increased (a volume ratio of 2:15:3:3, Experimental Example 4). As a result, the etching rates of Experimental Example 3 and Experimental Example 4 were approximately 1.26 μm/min and 8.14 μm/min, respectively. Both of the etching rates were high. Incidentally, 20 ml of the KI solution was also added in Experimental Examples 2-4 as with Experimental Example 1.

Table 1 provides a summary of the results mentioned above. Incidentally, every etching solution had a liquid temperature of 24±1° C. before conducting etching.

TABLE 1

| Etching Solution (Volume Ratio) | Etching Rate |
| --- | --- |
| Experimental Example 1 (1:15:3:3) | 1.54 μm/min |
| Experimental Example 2 (1:15:6:6) | 0.023 μm/min |
| Experimental Example 3 (1:30:3:3) | 1.26 μm/min |
| Experimental Example 4 (2:15:3:3) | 8.14 μm/min |
| Diluted Secco Solution | 0.065 μm/min |

Then, surfaces of the silicon wafers with low electrical resistivity which were etched with chromium-free etching solutions of Experimental Examples 2-4 were observed. An unsaturated oxide film or a stain film was not generated, and etch pits were observed on the etched wafer surfaces. However, except Experimental Example 2, the etching rates were so high that roughening of the etched wafer surfaces was generated. Consequently, it was difficult to detect crystal defects with stability. The present inventors experimented additionally. As a result, they have found that an etching rate greater than 100 nm of an etching solution to which KI solution is added tends to generate roughening of an etched wafer surface and it becomes difficult to detect crystal defects with stability.

Then, with regard to the etching solution of Experimental Example 2 (in a volume ratio of 1:15:6:6) whose etching rate was reduced sufficiently, the following experiment was conducted to confirm the dependence of a preventing effect of generating a stain film on KI concentration.

EXPERIMENT 2

First, 16.6 g of KI (0.1 mole) was dissolved into 1 liter of water to prepare KI solution. And the following etching solutions were prepared: 5 ml, 15 ml, or 20 ml of the KI solution was added respectively to 8 liters of a chromium-free etching solution in a volume ratio of 1:15:6:6. Weight of KI added to each etching solution was approximately 0.083 g, 0.249 g, and 0.332 g. Respective weights of KI contained per 1 liter of the 3 different etching solutions were calculated, and the weights were 0.010 g, 0.031 g, and 0.042 g, respectively.

Figure 3:
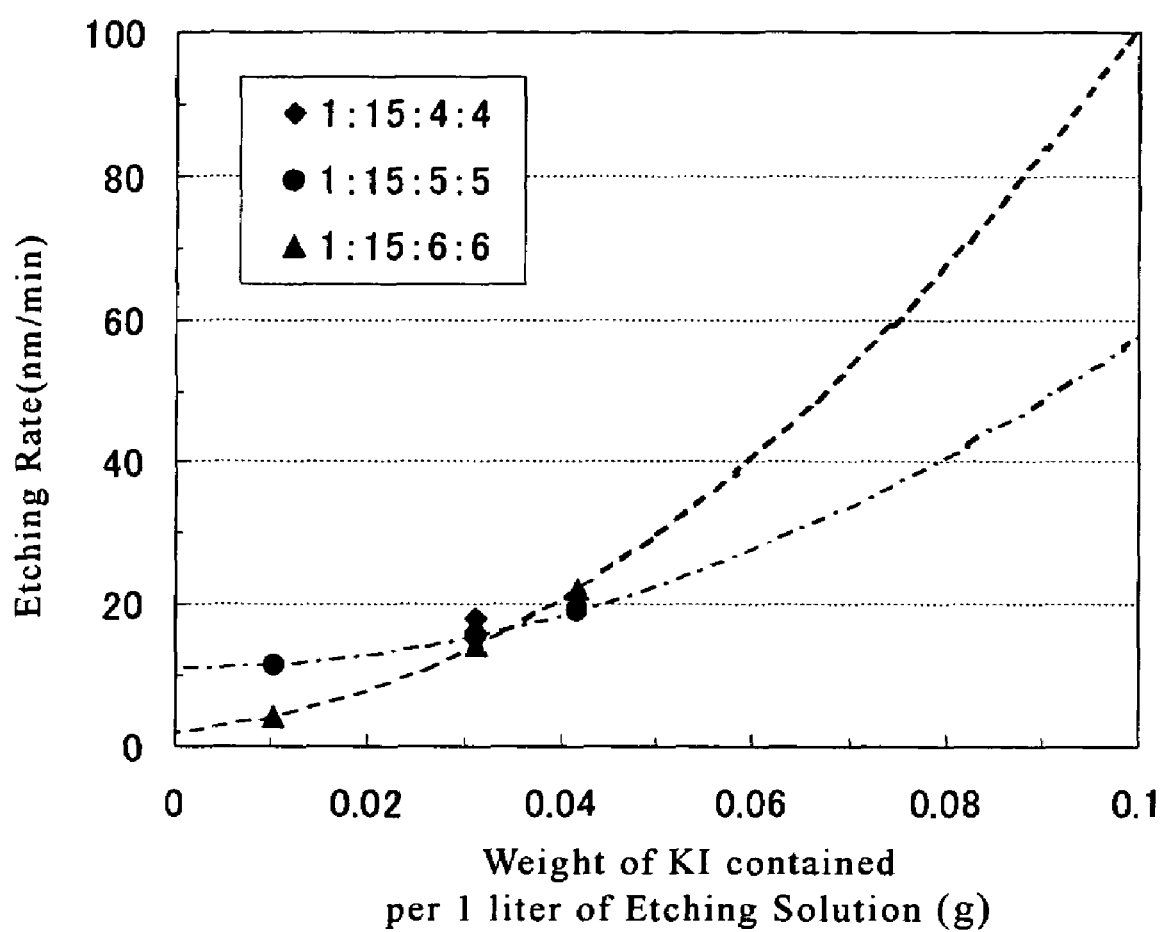
FIG. 3 is a graph in which a relationship between weight of KI contained per 1 liter of an etching solution and an etching rate is plotted.

Then, silicon wafers with low electrical resistivity were etched with thus prepared 3 different etching solutions as with Experiment 1. Etching rates of the 3 different etching solutions were measured. The conditions of etched wafer surfaces were observed. FIG. 3 is a graph in which a relationship between weight of KI contained per 1 liter of the etching solutions and etching rates is plotted. As is evident from FIG. 3, even a slight increase of weight of KI leads to a large increase of an etching rate.

KI is added to yield an effect of preventing generation of an unsaturated oxide film or a stain film. It has been confirmed that the effect was produced sufficiently in all the KI concentrations, and etch pits are detected with stability. At the same time, from the experimental results, it has been found that a slight addition of KI changes an etching rate significantly. This means that it is necessary to adjust an etching solution to have a prescribed etching rate (100 nm/min or less) in consideration of iodide concentration (content) when selective etching is conducted to a silicon wafer with low electrical resistivity by using an etching solution including hydrofluoric acid, nitric acid, acetic acid, water and iodide (or iodine).

Furthermore, with an etching solution in a volume ratio of 1:15:5:5, an experiment was conducted as with above with adding 5 ml, 15 ml, or 20 ml of the KI solution respectively. And the results of measuring etching rates were plotted in FIG. 3. Besides, as to an etching solution in a volume ratio of 1:15:4:4, an experiment was conducted only with the case of adding 15 ml of the KI solution. And the result of measuring an etching rate was also plotted in FIG. 3.

As shown in FIG. 3, it has been found that the etching solution in a volume ratio of 1:15:5:5 has also the dependence of an etching rate on KI concentration. Incidentally, it has been confirmed that, in both cases of etching silicon wafers with low electrical resistivity with the etching solution in a volume ratio of 1:15:5:5 and with the etching solution in a volume ratio of 1:15:4:4, an unsaturated oxide film or a stain film is not generated, and etch pits are observed with stability.

In summary of the above results, when the etching solution has a volume ratio of 1:15:4-6:4-6 and includes KI in a range from 0.01 g to 0.04 g per 1 liter of the etching solution, an etching rate certainly becomes 100 nm/min or less, in particular, 30 nm/min or less. And an unsaturated oxide film or a stain film is not generated, and it is possible to evaluate crystal defects with stability. Therefore, it has been found that such an etching solution is highly suitable for evaluating crystal defects of silicon wafers with low electrical resistivity.

Besides, an etching rate of an etching solution in a volume ratio of 1:15:8:8 to which 20 ml of the KI solution was added was measured separately. The etching rate was approximately 3 nm/min. Therefore, when the volume ratio of acetic acid and water in the etching solution is increased up to 1:15:8:8, an etching rate is decreased considerably. Such an etching solution is practical, for example, in the case of evaluating crystal defects in surface portion 100 nm or less deep from a silicon wafer surface, and so on. However, when the volume ratio of acetic acid and water is increased further and the etching rate is decreased further, etching wafers takes a long time and which is inefficient.

Furthermore, according to an approximate line obtained from values plotted on FIG. 3, it is estimated that an etching rate of an etching solution in the above volume ratio can be reduced certainly to 100 nm/min or less even when weight of KI to be contained in the etching solution is increased to 0.09 g. Then, a silicon wafer with low electrical resistivity was actually etched with an etching solution in a volume ratio of 1:15:6:6 to which 0.09 g of KI was added. Although etching rates of this etching solution varied more or less, every etching rate was 100 nm/min or less. On the other hand, when a wafer with low electrical resistivity is etched with the etching solution to which less than 0.01 g of KI is added, there is a possibility that an effect of preventing formation of an unsaturated oxide film or a stain film due to iodide is not provided sufficiently.

In summary, when the etching solution includes iodide (or iodine) in a range from 0.01 g to 0.09 g, generation of an unsaturated oxide film or a stain film can be prevented certainly. Moreover, an etching rate can be reduced to 100 nm/min or less, further to 50 nm/min or less, or 30 nm/min or less. Therefore, generation of roughening of an etched wafer surfaces can be prevented, and a removal amount of a wafer surface by etching can be controlled easily. As a result, etch pits formed on an etched surface of a wafer can be detected with an optical microscope etc. with stability, and crystal defects of a wafer can be evaluated accurately.

By the way, with changing the volume ratio of nitric acid, a silicon wafer was etched with an etching solution in which 5 ml of the KI solution used above was added to a mixture in a volume ratio of 1:18:6:6 (KI content was 0.010 g). Then, roughening of the etched wafer surface was generated, and it has been found that it can be difficult to evaluate crystal defects. In addition, when the volume ratio of nitric acid in the etching solution is reduced to less than 13, selectivity of etching is deteriorated and it can be difficult to evaluate crystal defects with sufficient sensitivity (capability of detecting defects). Therefore, it is judged that the volume ratio of nitric acid is preferably from 13 to 17.

Hereinafter, an embodiment of a method for evaluating crystal defects of a silicon wafer according to the present invention will be further described in detail. However, the present invention is not limited thereto.

A silicon wafer to be evaluated in the present invention has low electrical resistivity of 1 Ω·cm or less, in particular 0.001 to 1 Ω·cm. Conductivity type of the wafer may be p-type or n-type. Moreover, a method for producing the wafer is not limited particularly.

As an etching solution for detecting crystal defects in the vicinity of a surface of such a silicon wafer with low electrical resistivity, a method for evaluating crystal defects according to the present invention uses a mixture of hydrofluoric acid, nitric acid, acetic acid and water further including iodine or iodide.

To prepare such an etching solution, commercially available chemical solutions with semiconductor grade can be used. For example, hydrofluoric acid for semiconductor from DAIKIN INDUSTRIES, ltd. can be used as the hydrofluoric acid (concentration of 50 wt %); Class EL nitric acid from KANTO CHEMICAL CO., INC. can be used as the nitric acid (concentration of 61 wt %); and guaranteed acetic acid from KANTO CHEMICAL CO., INC. can be used as the acetic acid (concentration of 99.7 wt %). As for the water, ultrapure water used in semiconductor industries is preferably used in consideration of adhesion of particles, stain, etc. to a wafer during an etching process. As for the iodine or iodide, for example, an aqueous solution of solid iodine molecules ($I_2$) or potassium iodide (KI) is preferably prepared and added.

In preparing the etching solution, a mixture ratio of hydrofluoric acid, nitric acid, acetic acid and water is adjusted so that a volume ratio of nitric acid becomes the largest to enhance selectivity of etching, and an etching rate of a silicon wafer with low electrical resistivity becomes 100 nm/min or less. An etching rate of greater than 100 nm/min causes roughening of an etched wafer surface and then it becomes difficult to observe crystal defects with an optical microscope etc.

Specifically, the etching solution to be prepared preferably includes hydrofluoric acid nitric acid:acetic acid:water in a volume ratio of 1:13-17:4-8:4-8. The volume ratio of nitric acid less than 13 deteriorates selectivity of etching and it can be difficult to evaluate crystal defects with sufficient sensitivity. And, the volume ratio of nitric acid greater than 17 tends to cause roughening of an etched wafer surface and it can be difficult to observe etch pits after etching.

On the other hand, the volume ratio of acetic acid and/or water less than 4 in the etching solution increases an etching rate significantly. Then, it is estimated that controlling a removal amount by etching can be difficult, or roughening of an etched wafer surface tends to be generated. And such an etching solution can be unsuitable for etching of silicon wafers with low electrical resistivity. Conversely, the volume ratio of acetic acid and/or water greater than 8 decreases an etching rate too much. Then, etching wafers needs a long time, and it can be difficult to evaluate swiftly.

Furthermore, in the case of an etching solution with a low etching rate according to the present invention, the etching rate is influenced significantly by an addition amount of iodine or iodide, as mentioned above. Therefore, according to the present invention, it is necessary to adjust an addition amount of iodine or iodide to the etching solution so that the etching rate does not exceed 100 nm/min.

Specifically, it is preferable that the etching solution includes iodine or iodide in a range from 0.01 g to 0.09 g per 1 liter of total liquid volume of the etching solution. The etching solution including iodine or iodide in such a range certainly prevents generation of an unsaturated oxide film or a stain film in etching a silicon wafer with low electrical resistivity. Moreover, an etching rate can be reduced easily to 100 nm/min or less, further to 50 nm/min or less. Consequently, roughening of an etched wafer surface is not caused, and a removal amount of a surface of a silicon wafer by etching can be controlled easily.

Then, after an etching solution as mentioned above is adjusted, into thus adjusted etching solution a silicon wafer with low electrical resistivity to be evaluated is immersed to etch the wafer surface. At this time, it is preferable that a removal amount of the surface of the silicon wafer by etching is 50 nm or more. In this way when a silicon wafer is etched with a removal amount of the wafer surface by etching being 50 nm or more, etch pits originated from crystal defects can be formed on the wafer surface with stability.

After the silicon wafer is etched in this way, etch pits formed on the wafer surface are observed, for example, with an optical microscope etc. Thus crystal defects of the silicon wafer can be detected and evaluated with extreme accuracy and stability.

When crystal defects of a silicon wafer with low electrical resistivity is evaluated as mentioned above, an unsaturated oxide film or a stain film is not formed on a surface of the silicon wafer during etching. Moreover, selectivity of etching is high. Thus crystal defects in a silicon wafer with low electrical resistivity can be detected with excellent capability of detecting defects, and crystal defects can be evaluated accurately with stability. Furthermore, the etching solution does not contain chromium, and it is not necessary to consider the influence on the global environment and humans, wastewater treatment, and so on. Thus crystal defects can be evaluated easily and conveniently.

Hereinafter, the present invention will be explained further in detail with reference to Example and Comparative Example. However, the present invention is not limited thereto.

Example

Comparative Example

First, a p-type mirror-polished CZ silicon wafer with crystal orientation <100>, oxygen concentration of 14-18 ppma and low electrical resistivity of 0.001-0.02 Ω·cm was prepared. The silicon wafer was subjected to oxygen precipitation heat treatment at 800° C. for 4 hours and at 1000° C. for 16 hours under oxygen atmosphere to grow crystal defects in the wafer. Then, the silicon wafer which was treated with oxygen precipitation heat treatment was cleaved and split in two.

Crystal-defects density in the section of a half of the split wafer was measured with LST. (Thus measured crystal-defects density is defined as LST-defects density.) Then, the half was immersed in the chromium-free etching solution mentioned in Experiment 2 and including hydrofluoric acid:nitric acid:acetic acid:water in a volume ratio of 1:15:6:6 to which 20 ml of the KI solution was added (weight of KI contained per 1 liter of the etching solution was 0.042 g), and the half was etched for 4 minutes (Example). Moreover, another half of the split wafer was immersed in Wright solution diluted with pure water and was etched for 4 minutes (Comparative Example).

Figure 2:
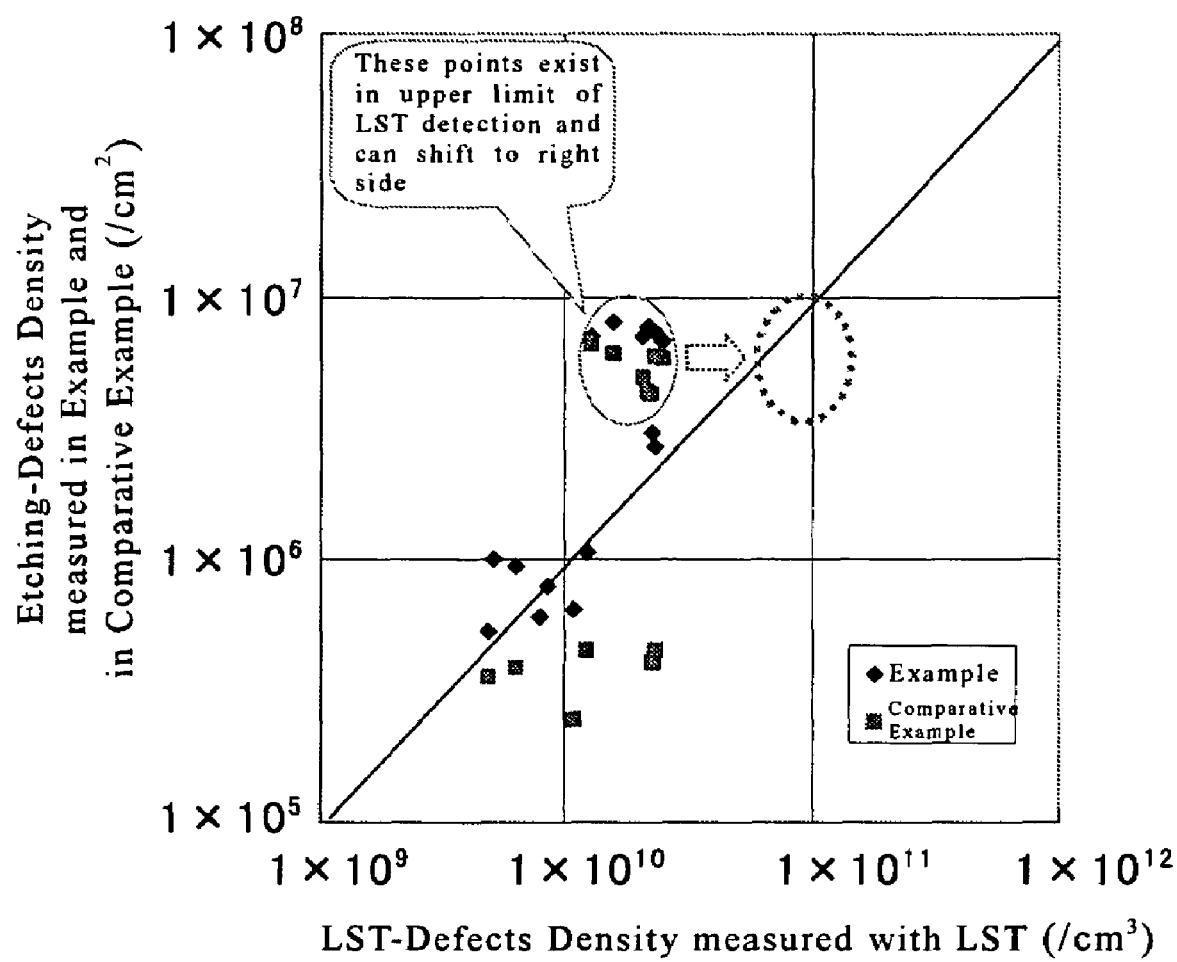
FIG. 2 is a graph in which a correlation between etching defects density measured in Example and in Comparative Example, and LST defects density measured with LST is plotted.

After the etching was conducted, each section of the cleaved silicon wafer was observed with an optical microscope (at a magnification of 500 times) to measure crystal-defects density. Incidentally, this crystal-defects density is defined as etching-defects density to be distinguished from the LST-defects density measured with LST. In FIG. 1, a correlation between etching-defects density measured after etching with the etching solution of Example and etching-defects density measured after etching with the Wright solution of Comparative Example is plotted. FIG. 2 is a graph in which a correlation between respective etching-defects density measured in Example and in Comparative Example, and LST-defects density measured with LST is plotted.

Incidentally, in FIG. 1, the square (■) shows number of stacking faults (SF); the diamond (♦) shows total number of stacking faults and Bulk Microdefect (BMD); the dot (●) shows total number of SF (Hereinafter, referred to as micro SF) which is larger than BMD but unable to be distinguished whether being SF or BMD), and BMD. In FIG. 2, the diamond (♦) shows a correlation between etching-defects density measured in Example and LST-defects density measured with LST before etching, and the square (■) shows a correlation between etching-defects density measured in Comparative Example and LST-defects density.

As is evident from FIG. 1, etching-defects density measured in Example according to an evaluating method of the present invention shows a strong correlation with etching-defects density in Comparative Example obtained by conventional etching with the Wright solution. Furthermore, as for total of crystal-defects density of BMD and micro SF (the dot (●)), it is confirmed that measured results of Example shows better sensitivity than those of Comparative Example. In summary, it is confirmed that a method for evaluating crystal defects according to the present invention has extremely high selectivity of an etching solution. And finer crystal defects which has conventionally been difficult to be detected can be detected easily with the method according to the present invention with high capability of detecting defects.

Furthermore, as is evident from FIG. 2, etching-defects density measured in Example also shows a strong correlation with LST-defects density measured by LST. In particular, current evaluation of crystal defects by LST has an upper limit of detection of LST-defects density of approximately $2 \times 10^{10}$/cm$^3$. However, as shown in FIG. 2, according to a method for evaluating crystal defects of the present invention, crystal defects of a wafer can be detected and evaluated with accuracy even when the wafer has crystal-defects density more than etching-defects density (approximately $2 \times 10^6$/cm$^3$) equivalent to the upper limit of detection of LST-defects density. Moreover, for example, LST-defects density more than the upper limit of detection can be obtained by extrapolation of a calibration curve showing a correlation between etching-defects density and LST-defects density.

The present invention is not limited to the embodiment described above. The above-described embodiment is mere an example, and those having substantially the same structure as technical ideas described in the appended claims and providing the similar functions and advantages are included in the scope of the present invention.

The invention claimed is:

1. A method for evaluating crystal defects of a silicon wafer comprising:
    evaluating crystal defects of a silicon wafer by selectively etching a surface of the silicon wafer by immersing the wafer in an etching solution and
    observing etch pits, which originated from crystal defects, formed on the etched surface of the wafer,
    wherein the silicon wafer of which crystal defects are evaluated has low electrical resistivity of 1 Ω·cm or less, and the etching solution is a mixture of hydrofluoric acid, nitric acid, acetic acid and water further including iodine or iodide, the etching solution having a volume ratio of hydrofluoric acid:nitric acid:acetic acid:water of 1:13-17:4-8: 4-8 and includes iodine or iodide in a range from 0.01 g to 0.09 g per 1 liter of total liquid volume of the etching solution to decrease the etching rate of the etching solution, and the etching solution is adjusted to have an etching rate of 100 nm/min or less for the silicon wafer.

2. The method for evaluating crystal defects of a silicon wafer according to claim 1, wherein a removal amount of the surface of the silicon wafer by etching is 50 nm or more.

* * * * *